United States Patent
Haran et al.

(10) Patent No.: US 11,235,173 B2
(45) Date of Patent: Feb. 1, 2022

(54) INTENSITY MODULATION DEVICE AND METHODS FOR RADIATION THERAPY, RADIATION SURGERY AND DIAGNOSTICS

(71) Applicants: Yossi Haran, Modi'in-Macabim-Re'ut (IL); Sigal Sela, Alon Hagalil (IL)

(72) Inventors: Yossi Haran, Modi'in-Macabim-Re'ut (IL); Sigal Sela, Alon Hagalil (IL)

( * ) Notice: Subject to any disclaimer, the term of this patent is extended or adjusted under 35 U.S.C. 154(b) by 0 days.

(21) Appl. No.: 16/492,168

(22) PCT Filed: Mar. 7, 2018

(86) PCT No.: PCT/IL2018/050268
§ 371 (c)(1),
(2) Date: Sep. 9, 2019

(87) PCT Pub. No.: WO2018/163179
PCT Pub. Date: Sep. 13, 2018

(65) Prior Publication Data
US 2020/0276452 A1    Sep. 3, 2020

Related U.S. Application Data

(60) Provisional application No. 62/467,948, filed on Mar. 7, 2017.

(51) Int. Cl.
*A61N 5/10* (2006.01)

(52) U.S. Cl.
CPC .......... *A61N 5/1042* (2013.01); *A61N 5/1048* (2013.01); *A61N 2005/1021* (2013.01); *A61N 2005/1095* (2013.01)

(58) Field of Classification Search
CPC .......... H01J 35/00; H01J 35/02; H01J 35/025; H01J 37/30; H01J 37/3002; H01J 37/304; H01J 37/3045; H01J 2237/04; H01J 2237/045; H01J 2237/0451; H01J 2237/0453; H01J 2237/0455; H01J 2237/083; H01J 2237/0835; A61N 5/10;
(Continued)

(56) References Cited

U.S. PATENT DOCUMENTS

| | | | | |
|---|---|---|---|---|
| 6,188,749 B1* | 2/2001 | Schiller | ..................... | G21K 1/10 378/156 |
| 7,652,273 B2* | 1/2010 | Cernasov | ................. | G21K 1/04 250/515.1 |

(Continued)

OTHER PUBLICATIONS

Sha Chang; "Compensator-Intensity-Modulated Radiotherapy—A Traditional Tool for Modern Application" European Oncological Disease 2006 2006;1(2):82-7, pp. 82-87.

(Continued)

*Primary Examiner* — Anastasia Midkiff
(74) *Attorney, Agent, or Firm* — Webb and Co. Ltd.; Chanoch Kahn

(57) ABSTRACT

A radiation beam intensity modulation device constituted of: a control circuitry; a plurality of cells, each of the plurality of cells arranged, responsive to the control circuitry, to be switched between an attenuating state and a transparent state; and attenuating material, each of the plurality of cells arranged to contain therewithin a portion of the attenuating material when in the attenuating state and not contain therewithin the portion of the attenuating material when in the transparent state.

19 Claims, 4 Drawing Sheets

(58) Field of Classification Search
CPC .. A61N 5/1042; A61N 5/1045; A61N 5/1048; A61N 5/1064; A61N 5/1065; A61N 5/1067; A61N 5/1077; A61N 2005/1021; A61N 2005/1092–5; G21K 1/00; G21K 1/02; G21K 1/025; G21K 1/04; G21K 1/043; G21K 1/046; G21K 1/08; G21K 1/087; A61B 6/00; A61B 6/06; A61B 6/08; A61B 6/40; A61B 6/4035; A61B 6/405; G01J 5/08; G01J 5/0806; G01J 5/0812; G01J 5/0831; G01J 5/0834; G01J 5/084; G01J 5/085; G01J 5/0862; G01J 5/0871; G02F 1/00; G02F 1/0009; G02F 1/0018; G02F 1/0063; G02F 1/01; G02F 1/0102; G02F 1/0107; G02F 1/165; G02F 1/1679; G02F 1/1681; G02F 1/1685; G02F 1/17; G02F 2201/08; G02F 2203/0012; G02F 2203/24; G02F 2203/52; G02B 1/00; G02B 1/002; G02B 1/06; G02B 5/00; G02B 5/005; G02B 5/20; G02B 5/201; G02B 5/204; G02B 5/22; G02B 5/24; G02B 7/00; G02B 7/006; G02B 26/00; G02B 26/004; G02B 26/02; G02B 26/023; G02B 26/04; G02B 27/00; G02B 27/0006; G02B 27/09; G02B 27/0927; G02B 27/0933; G02B 27/0938; G02B 27/0988; G02B 27/30; G02B 30/00; G02B 2207/121; G05B 11/14; G05B 11/18; G05B 11/32; G05B 15/02; G05B 21/02

See application file for complete search history.

(56) References Cited

U.S. PATENT DOCUMENTS

| | | | |
|---|---|---|---|
| 8,129,701 B2* | 3/2012 | Al-Sadah | A61N 5/1042 250/505.1 |
| 2003/0198319 A1* | 10/2003 | Toth | G21K 1/10 378/159 |
| 2007/0040127 A1 | 2/2007 | Brahme et al. | |
| 2014/0110604 A1 | 4/2014 | Ein-Gal | |
| 2016/0059040 A1 | 3/2016 | Paliwal et al. | |
| 2016/0113617 A1* | 4/2016 | Herrmann | A61B 6/582 378/207 |

OTHER PUBLICATIONS

International Search Report for PCT/IL2018/050268 issued by USPTO dated Jul. 6, 2018.
Written Opinion of the International Searching Authority for PCT/IL2018/050268 issued by USPTO dated Jul. 6, 2018.

* cited by examiner

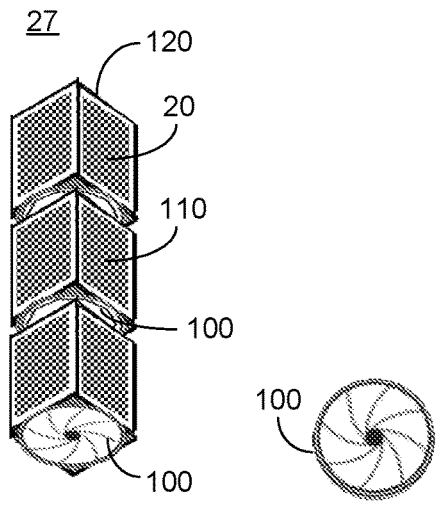
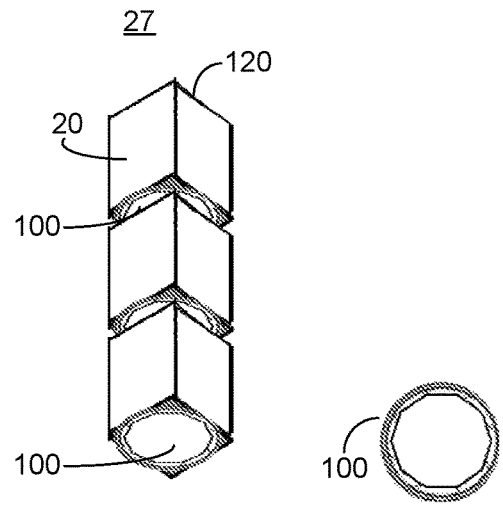
FIG. 4A    FIG. 4B    FIG. 5A    FIG. 5B
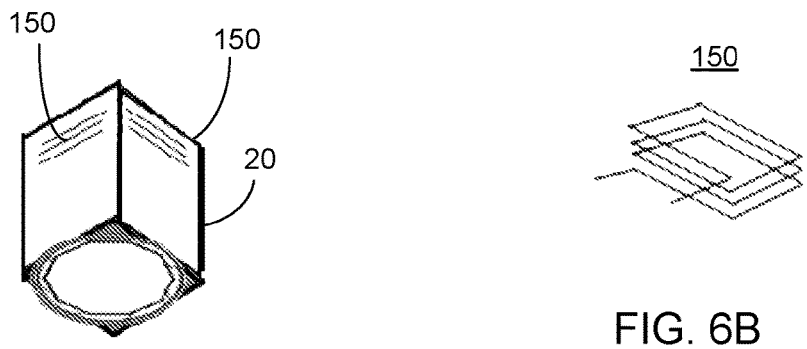
FIG. 6A    FIG. 6B

INTENSITY MODULATION DEVICE AND METHODS FOR RADIATION THERAPY, RADIATION SURGERY AND DIAGNOSTICS

CROSS-REFERENCE TO RELATED APPLICATIONS

This application claims priority from U.S. provisional patent application Ser. 62/467,948, filed Mar. 7, 2017 and entitled "INTENSITY MODULATION DEVICE AND METHODS FOR RADIATION THERAPY, RADIATION SURGERY AND DIAGNOSTICS", the entire contents of which are incorporated herein by reference.

TECHNICAL FIELD

The invention relates generally to the field of external beam radiation therapy and more particularly to an Intensity Modulation method and device for Intensity Modulated Radiation Therapy (IMRT).

BACKGROUND

Intensity modulated radiation therapy (IMRT) is a well-established method for dose distribution to the target volume while sparing nearby organs at risk and healthy tissues.

The process includes treatment planning systems that optimize the intensity distribution of the delivered beam, accelerators that deliver external beams and a beam modulator/shaper.

Several techniques for intensity modulating of beams have been developed, one commonly in use is the multi-leaf collimators (MLCs). In this technique, sometimes called "Segmental IMRT", the intensity modulated beam is achieved by the delivery of segment after segment for the delivery of a planned intensity map.

Segmental IMRT has 3 main Drawbacks:
1. The total treatment time is significantly extended.
2. The time differential in the delivery of segments creates a shifted output (hot and cold spots).
3. The segmental delivery method can't be applied to constantly moving tumors.

In an alternative technique, sometimes called "IMRT compensators", the intensity modulated beam is achieved by placing a pre-manufactured compensator between the beam and the target and the planned intensity map is irradiated simultaneously.

This technique of simultaneous complete intensity map irradiation results has an improved outcome compared to sequential delivery of the dose segments.

IMRT compensators have 2 main drawbacks:
1. A pre-manufacturing process is necessary for each patient and each beam.
2. The exchange to different compensators between beams is manual.

What is desired is a radiation therapy technique which overcomes at least part of the disadvantages of the prior art.

SUMMARY OF THE INVENTION

Accordingly, it is a principal object of the present invention to overcome disadvantages of prior art methods and arrangements of radiation therapy. This is provided in the present invention by a radiation beam intensity modulation device constituted of: a control circuitry; a plurality of cells, each of the plurality of cells arranged, responsive to the control circuitry, to be switched between an attenuating state and a transparent state; and attenuating material, each of the plurality of cells arranged to contain therewithin a portion of the attenuating material when in the attenuating state and not contain therewithin the portion of the attenuating material when in the transparent state.

In one embodiment, each of the plurality of cells exhibits a mechanical opening, arranged responsive to the control circuitry to switch between an open state where the attenuating material can pass therethrough and a closed state where the attenuating material cannot pass therethrough. In one further embodiment, the attenuating material is immersed in a fluid, the fluid arranged to pass through the mechanical opening in both the open and closed state.

In another embodiment, the plurality of cells comprises a plurality of columns cells thereby forming a 3 dimensional array. In one further embodiment, the plurality of columns are filled with the attenuating material in parallel.

In one embodiment, each of the plurality of cells comprises an electric coil, the control circuitry arranged to sense an indication of attenuating material in the respective cell responsive to inductive properties of the electric coil. In another embodiment, the device further comprises a radiation sensor arranged to sense an intensity map of a radiation beam output through the plurality of cells.

In one embodiment, the device further comprises: an entry aperture; and an exit aperture, wherein a height of the cells closer to the entry aperture is less than a height of the cells closer to the exit aperture, the height defined between the entry aperture and the exit aperture.

In one independent embodiment, a radiation beam intensity modulation method is provided, the method comprising alternately switching each of a plurality of cells between an attenuating state and a transparent state, each of the plurality of cells arranged to contain therewithin a respective portion of attenuating material when in the attenuating state and not contain therewithin the respective portion of the attenuating material when in the transparent state.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 4A illustrates a high level perspective view of a section of a column of cells of FIG. 2A in an attenuating state, according to certain embodiments;

FIG. 4B illustrates a high level top view of a cell iris in a closed state, according to certain embodiments;

FIG. 5A illustrates a high level perspective view of a section of a column of cells of FIG. 2A in a transparent state, according to certain embodiments;

FIG. 5B illustrates a high level top view of a cell iris in an opened state, according to certain embodiments;

FIG. 6A illustrates a high level perspective view of a cell of FIG. 2A comprising an electric coil, according to certain embodiments;

FIG. 6B illustrates a high level perspective view of the electric coil of FIG. 6A, according to certain embodiments;

DETAILED DESCRIPTION OF THE PREFERRED EMBODIMENTS

Figure 1:
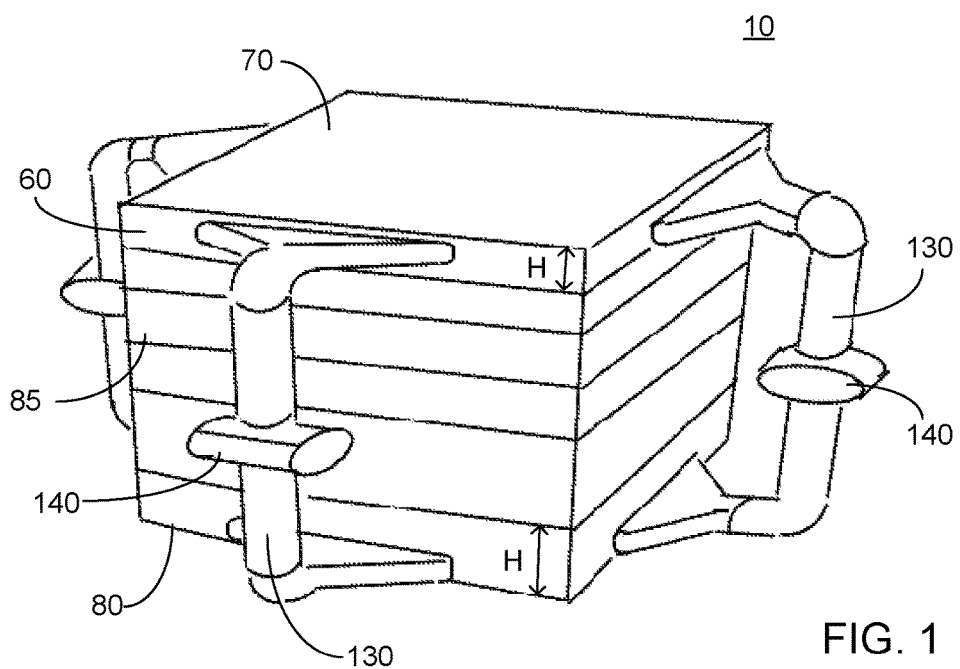
FIG. 1 illustrates a high level perspective view of a beam modulation device, according to certain embodiments.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

This is provided by a system and method for control of radiation therapy delivery, according to certain embodiments. FIGS. 1-8 are described together. Particularly, as illustrated in FIG. 1, a beam modulation device 10 is provided which utilizes a 3-dimensional (3D) array of radiation attenuating cells 20 to enable real time setting and simultaneous delivery of a complete intensity map. In one embodiment, beam modulation device 10 enables simultaneous delivery of a complete intensity map of a planned beam orientation.

Figure 2A:
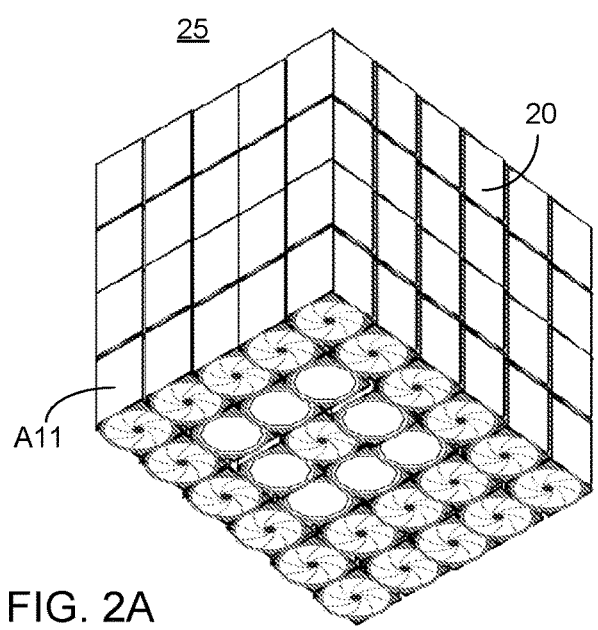
FIG. 2A illustrates a high level perspective view of a 3 dimensional (3D) array of cells, according to certain embodiments.

Beam modulation device 10 comprises a plurality of cells 20, preferably arranged in a 3D array 25, as illustrated in FIG. 2A. Each cell 20, responsive to a control circuitry 30, is arranged to alternately switch its radiation attenuating state between a transparent state, where radiation passing therethrough is not substantially attenuated, and an attenuating state, where radiation passing therethrough is attenuated by a predetermined amount, as will be described below. Thus, responsive to control circuitry 30, a customized radiation attenuating block is created, optionally in real time. Consequently, a radiation beam 40 entering the 3D cell array 25 at a uniform intensity becomes an intensity modulated beam upon exiting it, as described below in relation to FIG. 3. As described above, each cell 20 in the array is arranged, responsive to control circuitry 30, to switch its radiation attenuating state between two states:

1. Transparent state—the cell 20 is fully transparent to radiation beam 40 and does not significantly attenuate radiation beam 40.
2. Attenuating state—the cell 20 is arranged to attenuate radiation beam 40 in accordance with its physical properties (i.e. the cell height, cell density and type of attenuating material within the cell 20).

Figure 2B:
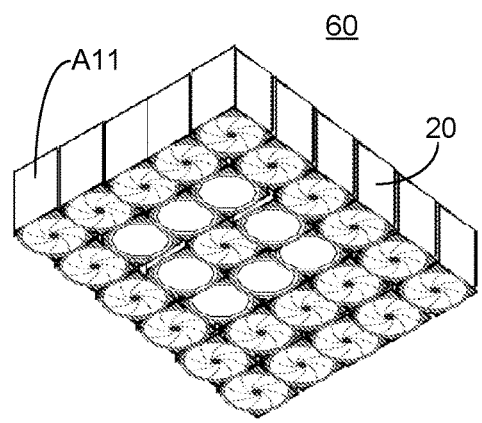
FIG. 2B illustrates a high level perspective view of one layer of the 3D array of cells of FIG. 2A.
Figure 3:
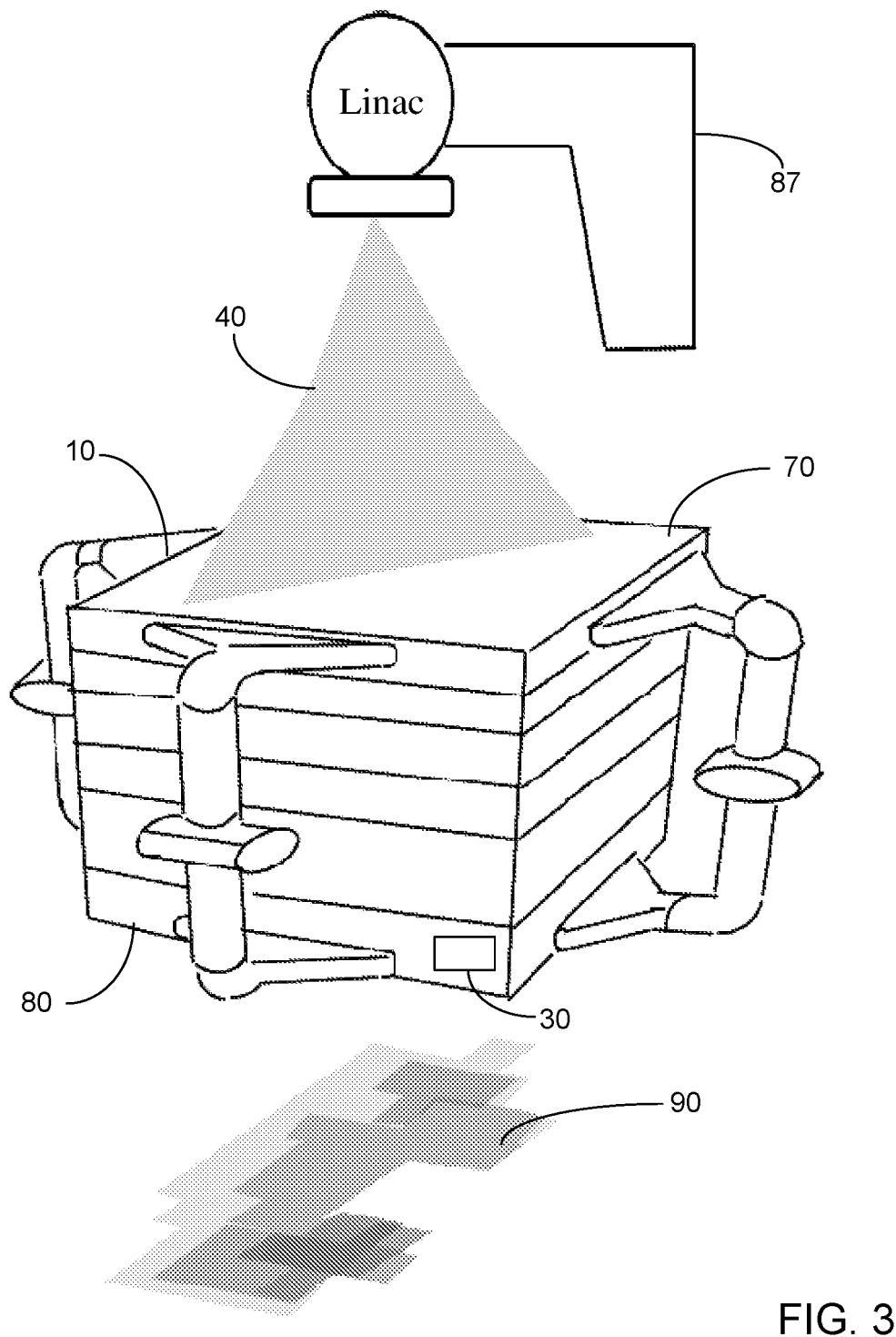
FIG. 3 illustrates a high level perspective view of a radiation beam passing through the beam modulation device of FIG. 1, according to certain embodiments.

As illustrated in FIGS. 2A-2B, cells 20 are organized in layers 60, stacked one on top of the other. Particularly, FIG. 2B illustrates a single layer 60 in the array of cells 20. For example, one corner cell 20 is denoted A11, i.e. the cell 20 of column 1 in row 1. FIG. 2A illustrates a plurality of arrays of cells 20 stacked on top of each other thereby forming 3D array 25. In one non-limiting embodiment, 3D array 25 is a cube. Beam modulation device 10 exhibits an entry aperture 70, an exit aperture 80 and a cell area 85 containing cell array 25. As illustrated in FIG. 3, entry aperture 70 of beam modulation device 10 is juxtaposed with a radiation beam device 87, radiation beam device 87 arranged to output radiation beam 40. Exit aperture 80 of beam modulation device 10 is juxtaposed with a target tissue (not shown). The intensity level of radiation beam 40 exiting array 25 is responsive to the number of cells 20 in the attenuating state which radiation beam 40 passed through in array 25 and their attenuation properties. As illustrated in FIG. 3, radiation beam 40 is irradiated through beam modulation device 10. The cells 20 in the attenuation state attenuate radiation beam 40 thereby outputting an intensity map 90.

Transforming Mechanism—each cell 20 in array 25 contains a mechanism for switching between the attenuating state and the transparent state. In one non-limiting embodiment, a (0) state is the transparent state and a (1) state is the attenuating state. In one embodiment, the transforming mechanism comprises an electro-mechanic gate 100, preferably shaped as an iris, and described herein as such, as illustrated in FIGS. 4A-4B and 5A-5B. Each electro-mechanic gate 100 is in communication with control circuitry 30. Particularly, FIG. 4A illustrates a high level perspective view of a column 27 of cells 20 in the attenuating state. As will further be described below, cells 20 are in the attenuating state responsive to the iris 100 of the bottommost cell 20 of the column. FIG. 4B illustrates iris 100 in the closed state. As will be described below, when closed, iris 100 doesn't allow attenuating material 110 to exit, thereby capturing attenuating material 110 within the cell 20. Particularly, the attenuating state of a cell 20 is defined as the state where an iris 100 within the cell column 27, below the respective cell 20, is closed and the cell 20 contains attenuating material 110. When electro-mechanic iris 100 is opened, as illustrated in FIGS. 5A-5B, the attenuating material 110 within the cell is released. Particularly, the transparent state of a cell 20 is defined as the state where all the irises 100 in the column 27 below the respective cell 20 are opened and the respective cell 20 does not contain attenuating material 110. Cell further exhibits an opening 120, juxtaposed with iris 100. Cell openings 120 are juxtaposed with entry aperture 70 of beam modulation device 10 and irises 100 are juxtaposed with exit aperture 80 of beam modulation device 10 such that a plurality of columns 27 of cells 20 are contained within beam modulation device 10, iris 100 of each cell 20 arranged to mate with opening 120 of an adjacent cell 20 in the respective column 27.

Transportation and delivery mechanism the transportation and delivery mechanism inserts attenuating material 110 into cells 20 and evacuates attenuating material 110 exiting cells 20. Particularly, in one embodiment attenuating material 110 is immersed in a fluid. Optionally, attenuating material 110 comprises tungsten powder and the fluid comprises oil, preferably of a low viscosity. In one embodiment, the viscosity of the oil is less than 0.5 pas. In one embodiment, a plurality of tubular members 130 are provided, each tubular member 130 having stored therein attenuating material 110 and the immersion fluid. A plurality of centrifugal pumps 140 are additionally provided, each centrifugal pump 140 positioned within a respective tubular member 130. In stage 1000 of FIG. 8, centrifugal pumps 140 are arranged to pump the fluid, containing attenuating material 110, into cell area 85. The pumped fluid enters cells 20 at the vicinity of entry aperture 70 such that the fluid enters each cell column 27 through opening 120 of the cell 20 closest to entry aperture 70. In one embodiment, centrifugal pumps 140 are arranged such that the fluid enters cell columns 27 in parallel in time, i.e. cell columns 27 are filled together and not filled sequentially. In another embodiment, centrifugal pumps 140 are arranged such that a generally equal portion of fluid generally simultaneously enters each of the columns 27. In one embodiment, two tubular members 130, opposing each other, are arranged to pump the attenuating material 110 and fluid into cell area 85. In another embodiment, four tubular members 130 are provided, a first pair of tubular members 130 arranged to pump fluid immersed attenuating material 110 into cell area 85 and a second pair of tubular members 130 arranged to pump fluid not containing attenuating material 110 into cell area 85. The fluid not containing attenuating material, i.e. "clean" fluid, is arranged to clean any residual attenuating material 110 from the vicinity of cells 20. Thus, for each column 27, each cell 20 is arranged to be in fluid communication with an adjacent cell 20 of the respective column 27. The term "fluid communication", as used herein, means that fluid can pass therebetween.

In stage 1010, control circuitry 30 is arranged to determine, responsive to a predetermined intensity map, how many cells 20 in each column 27 need to be in the attenuating state. Control circuitry 30 is then arranged to close iris 100 of a particular cell 20 in each column 27 such that the appropriate number of cells 20 are filled with attenuating material 110, thus creating a 3D compensator. For example, if 3 cells 20 of a column 27 need to be filled with attenuating material 110, iris 100 of the third cell 20 is closed thereby causing the 3 cells 20 closest to entry aperture 70 to be filled with attenuating material, as illustrated in FIG. 4A. In one embodiment, irises 100 are arranged such that, when in a closed state, attenuating material 110 cannot pass therethrough, however the immersion fluid can pass therethrough.

Thus, cell array 25 constitutes an IMRT cube presenting a real-time dynamic compensator based on a 3D array of attenuating cells 20. Particularly, a patient can be brought into the treatment room and the intensity map, determined earlier or during the present session, can be entered into the control circuitry. The control circuitry is then arranged to switch the respective cells into the attenuating state according to the entered intensity map, thereby providing a real-time dynamic compensator based on a 3D array of radiation attenuating cells 20. When radiation beam 40, exhibiting a uniform intensity, enters beam modulation device 10 at the entry aperture 70, the exiting radiation at exit aperture 80 becomes intensity modulated responsive to the number of cells 20 in the attenuating state that the radiation beam has passed through, as described above.

In one embodiment, as illustrated in FIG. 1, cells 20 positioned closer to entry aperture 70 have a smaller height, denoted H, than cells 20 positioned closer to exit aperture 80. As radiation beam 40 enters through entry aperture 70, the intensity is at the maximum value. As a result, a smaller amount of attenuation material 110 is needed for attenuation of radiation beam 40 since the probability of collision between photons, or other radiation particles, and attenuating material 110 is high due to the high intensity. As the intensity of radiation beam 40 decreases due to passing through cells 20 in the attenuating state, the probability of collision between the radiation and the attenuating material 110 decreases and more attenuating material 110 is necessary for attenuating radiation beam 40. Therefore, cells 20 which are reached by radiation beam 40 after passing through other cells 20 have an increased height H to thereby have more attenuating material 110 stored therein, thus allowing attenuation of lower intensity radiation.

In another embodiment (not shown), cells 20 near the center of cell array 25 exhibit a smaller cross section than cells 20 near the borders of cell array 25, i.e. center cells 20 are smaller than outer cells 20, thereby providing increased resolution at the center of the intensity map.

In one embodiment, as illustrated in FIGS. 6A-6B, one or more walls of each cell 20 comprises an electric coil 150 in electrical communication with control circuitry 30. The inductive properties of electric coil 150 change responsive to the radiation attenuating material 110 being contained inside cell 20. As a result, in optional stage 1020, control circuitry 30 is arranged, after the respective cells 20 have been switched to the attenuating state and filled with attenuating material 110, to identify the properties of each electric coil 150 and determine responsive thereto if a cell 20 contains attenuating material 110 and how much it contains.

Figure 7:
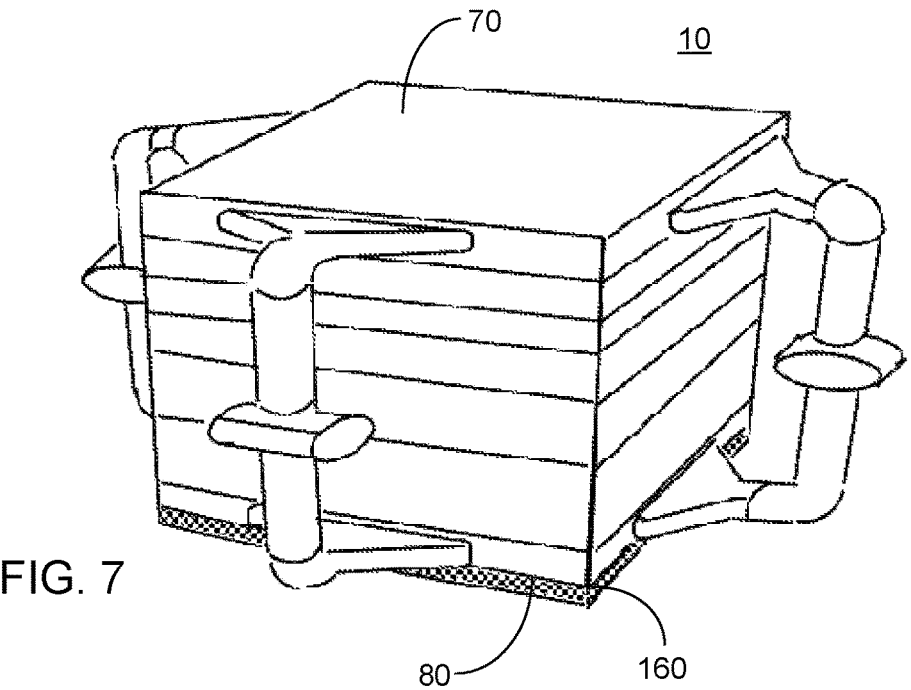
FIG. 7 illustrates a high level perspective view of the beam modulation device of FIG. 1, further comprising an array of radiation sensors, according to certain embodiments.
Figure 8:
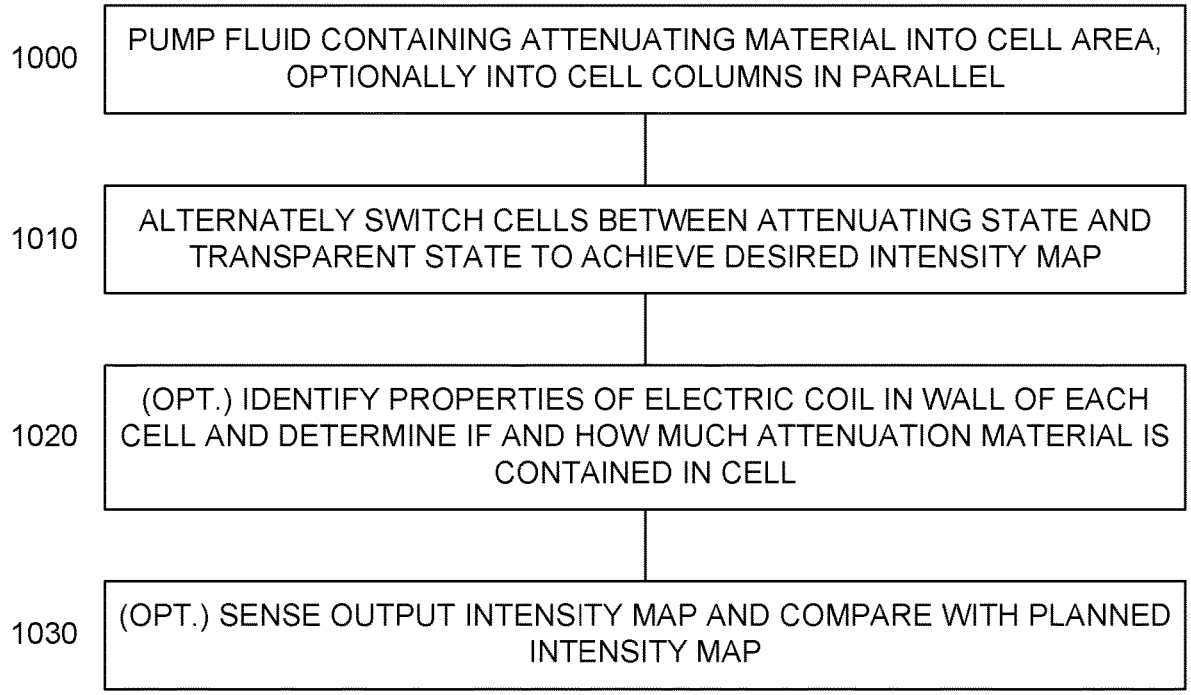
FIG. 8 illustrates a high level flow chart of a radiation beam modulation method, according to certain embodiments.

In another embodiment, as illustrated in FIG. 7, an array of radiation sensors 160 is positioned at exit aperture 80 of beam modulation device 10. In one embodiment, radiation sensor array 160 comprises a flat panel detector. In operation, in optional stage 1030, after cells 20 are switched into the respective attenuating and transparent states, a 1 monitor unit radiation beam is output through cell area 85. Radiation sensor array 160 is arranged to sense the output intensity map and 30 control circuitry is arranged to compare the sensed intensity map with the planned intensity map. If the sensed intensity map matches the planned intensity map, within a predetermined error value, the target tissue is irradiated according to the predetermined treatment plan. In the event of a discrepancy between the sensed intensity map and the planned intensity map, in one embodiment, the transportation and delivery mechanism is arranged to again pump the fluid, containing the attenuating material 110, through cells 20 such that the appropriate cells 20 are filled. In another embodiment, control circuitry 30 is arranged to open all irises 100, thereby emptying the attenuating material 110 from cells 20, and the above described process of filling the selected cells 20 is again performed. Optionally, irradiation treatment is initiated only if both: control circuitry 30 determines via electric coil sensors 150 that all of the cells 20 which are supposed to be in the attenuating state contain attenuating material 110 and all the cells 20 which are supposed to be in the transparent state do not contain attenuating material 110; and the sensed intensity map matches the planned intensity map.

Advantageously, the above embodiments may further allow for improved diagnostics. In certain embodiment, imaging of a target, while protecting nearby critical organs is provided. Thus cells 20 in the path of the target are set to the transparent state, and other cells 20, particularly those in line between the diagnostic radiation source and critical organs, are set to the attenuating state. The present embodiments thus advantageously reduces the undesired radiation experienced by the patient by using the intensity modulation device of the present embodiments to adjust the intensity of the diagnostic beam by determining, and implementing, the proper setting for each of the cells based on the expected attenuation along the track from the source to the detectors in relation to the specific angular and human autonomy along the track so as to meet a planned intensity map.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

The terms "include", "comprise" and "have" and their conjugates as used herein mean "including but not necessarily limited to".

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

The invention claimed is:

1. A radiation beam intensity modulation device comprising:
   a control circuitry; and
   a 3 dimensional (3D) array of cells,
   wherein said control circuitry is arranged to control each cell of said 3D array of cells to be switched between an attenuating state and a transparent state,
   wherein, in said attenuating state, each of said cells attenuates radiation by a predetermined amount,
   wherein, in said transparent state, said respective cell each of said cells does not substantially attenuate radiation,
   wherein said 3D array of cells comprises a 2 dimensional (2D) array of columns of said cells, each of said columns of said cells comprising a respective plurality of said cells, and
   wherein, for each of said columns of said cells, each cell is arranged to be in fluid communication with an adjacent cell of the respective column.

2. The device of claim 1, further comprising attenuating material, each cell of said 3D array of cells arranged to contain therewithin said attenuating material when in said attenuating state and not contain therewithin said attenuating material when in said transparent state.

3. The device of claim 2, wherein each cell of said 3D array of cells exhibits a mechanical opening, arranged responsive to said control circuitry to switch between an open state where said attenuating material can pass therethrough and a closed state where said attenuating material cannot pass therethrough.

4. The device of claim 3, wherein said attenuating material is immersed in a fluid, said fluid arranged to pass through said mechanical opening in both said open and closed state.

5. The device of claim 3, further comprising:
   an entry aperture; and
   an exit aperture,
   wherein, for each of said columns, each of said cells of said respective column is switched to said transparent state responsive to:
   said mechanical opening of said respective cell being switched to said open state; and
   said mechanical openings of all cells of said respective column, between said respective cell and said exit aperture, being switched to said open state.

6. The device of claim 5, wherein, for each of said columns, each of said cells of said respective column is switched to said attenuating state responsive to said mechanical opening of one of said cells of said respective column, between said respective cell and said exit aperture, being switched to said closed state.

7. The device of claim 1, further comprising:
   an entry aperture; and
   an exit aperture,
   wherein a height of said cells closer to said entry aperture is less than a height of said cells closer to said exit aperture, said height defined between said entry aperture and said exit aperture.

8. A radiation beam intensity modulation method, the method comprising alternately switching each cell of a 3 dimensional (3D) array of cells between an attenuating state and a transparent state,
   wherein, in the attenuating state, each of the cells attenuates radiation by a predetermined amount,
   wherein, in the transparent state, each of the cells does not substantially attenuate radiation,
   wherein the 3D array of cells comprises a 2 dimensional (2D) array of columns of the cells, each of said columns of the cells comprising a respective plurality of the cells, and
   wherein, for each of the columns of the cells, each cell is arranged to be in fluid communication with an adjacent cell of the respective column.

9. The method of claim 8, wherein each cell of the 3D array of cells is arranged to contain therewithin attenuating material when in said attenuating state and not contain therewithin attenuating material when in said transparent state.

10. The method of claim 8, wherein each cell of the array of cells is arranged to contain therewithin attenuating material when in said attenuating state and not contain therewithin attenuating material when in said transparent state, and
    wherein the method further comprising filling the columns of the cells with said attenuating material in parallel.

11. A radiation beam intensity modulation device comprising:
    a control circuitry;
    a 3 dimensional (3D) array of cells, each cell of said array of cells arranged, responsive to said control circuitry, to be switched between an attenuating state and a transparent state; and
    attenuating material, each of said cells arranged to contain therewithin said attenuating material when in said attenuating state and not contain therewithin said attenuating material when in said transparent state, wherein the 3D array of cells comprises a 2 dimensional (2D) array of columns of the cells, each of said columns of the cells comprising a respective plurality of the cells, and wherein, for each of the columns of the cells, each cell is arranged to be in fluid communication with an adjacent cell of the respective column.

12. The device of claim 11, wherein, in said attenuating state, each of said cells attenuates radiation by a predetermined amount, and wherein, in said transparent state, each of said cells does not substantially attenuate radiation.

13. The device of claim 2, wherein said attenuating material is immersed in a fluid, and wherein each of said columns of said cells presents a respective path such that the fluid can flow through the respective column.

14. The device of claim 11, wherein said attenuating material is immersed in a fluid, and wherein each of said columns of said cells presents a respective path such that the fluid can flow through the respective column.

15. The device of claim 11, wherein each cell of said 3D array of cells exhibits a mechanical opening, arranged responsive to said control circuitry to switch between an open state where said attenuating material can pass therethrough and a closed state where said attenuating material cannot pass therethrough.

16. The device of claim 15, wherein said attenuating material is immersed in a fluid, said fluid arranged to pass through said mechanical opening in both said open and closed state.

17. The device of claim 1, wherein, in said attenuating state, each of said cells attenuates radiation by a fixed predetermined amount.

18. The device of claim 8, wherein, in said attenuating state, each of the cells attenuates radiation by a fixed predetermined amount.

19. The device of claim 11, wherein, in said attenuating state, each of said cells is arranged to contain therewithin a fixed predetermined amount of said attenuating material.

* * * * *